United States Patent [19]  
Lather et al.

[11] 4,147,065  
[45] Apr. 3, 1979

[54] ULTRASONIC TESTING

[75] Inventors: Dieter Lather, Rheurdt; Klaus-Uwe Janssen, Lintorf; Karl Ries, Mülheim; Peter Möller, Wuppertal; Ulrich Forstermann, Sprockhoevel, all of Fed. Rep. of Germany

[73] Assignees: Mannesmann AG., Dusseldorf; Karl Deutsch Pruf-und Messgeratebau, Wuppertal-Elberfeld, both of Fed. Rep. of Germany

[21] Appl. No.: 775,159

[22] Filed: Mar. 7, 1977

[30] Foreign Application Priority Data

Mar. 10, 1976 [DE] Fed. Rep. of Germany ....... 2610457

[51] Int. Cl.² ........................................... G01N 29/04
[52] U.S. Cl. ..................................... 73/611; 73/615
[58] Field of Search ................ 73/67.9, 611, 614, 612, 73/615, 616

[56] References Cited

U.S. PATENT DOCUMENTS 3,942,358  3/1976  Pies ................................. 73/67.9 X
3,986,389  10/1976  Mesina et al. ....................... 73/67.9

FOREIGN PATENT DOCUMENTS 166160  5/1965  U.S.S.R. .............................. 73/67.9

Primary Examiner—Stephen A. Kreitman
Attorney, Agent, or Firm—Smyth, Pavitt, Siegemund, Jones & Martella

[57] ABSTRACT

Ultrasonic echo signals from the rear wall boundary are used to track looking windows for similar signals during a subsequent test cycle as well as for detection of flaw echos, with emphasis on a distinction between end of flaw detection and beginning first rear wall echo looking windows.

4 Claims, 2 Drawing Figures

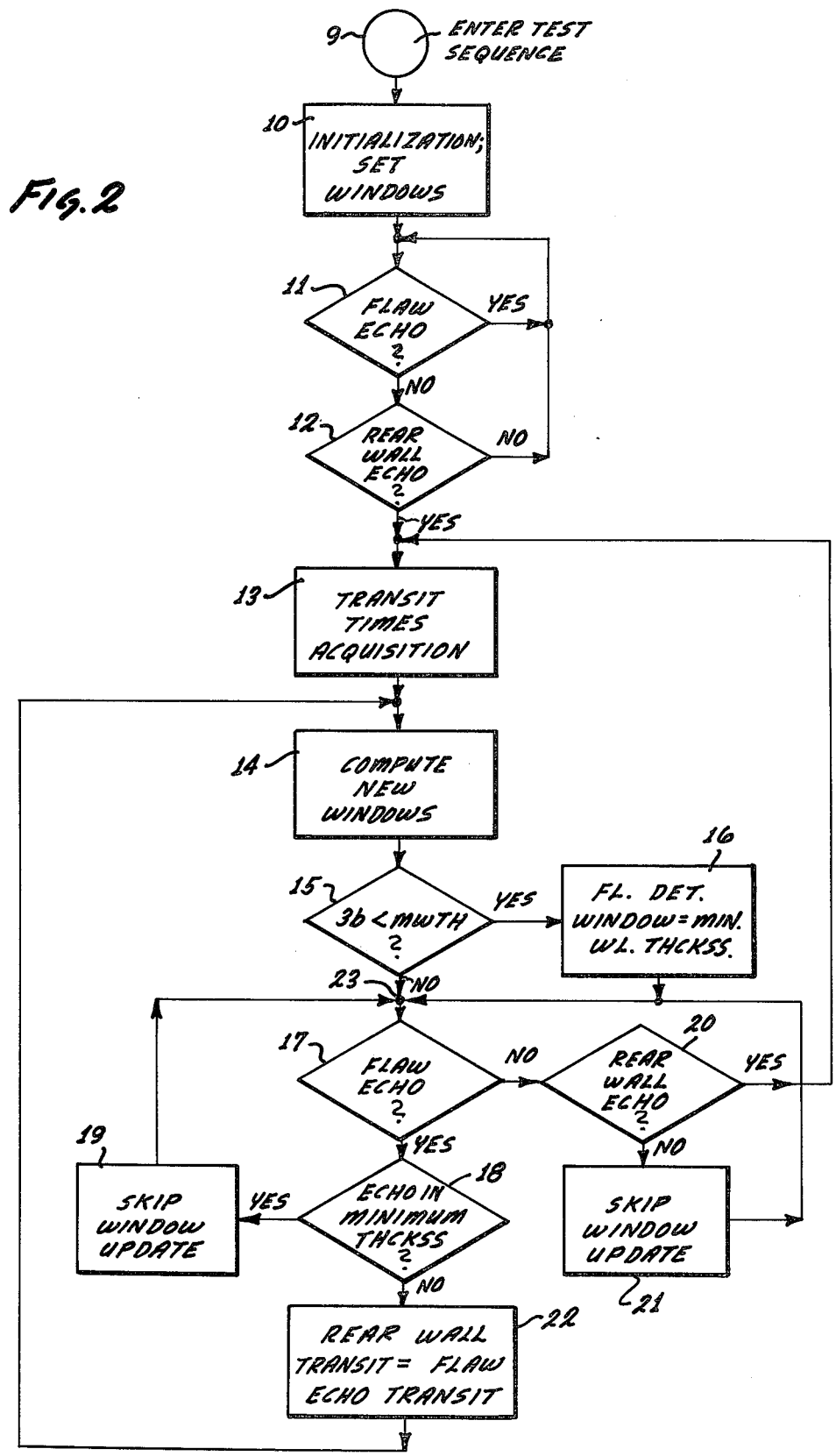

ULTRASONIC TESTING

BACKGROUND OF THE INVENTION

The present invention relates to automatically adjusting the looking window for the detection of ultrasonic signals, by means of follow-up control.

The "looking window" referred to above is to mean, for example, the period during which an ultrasonic receiver is enabled to receive an echo signal. A looking window, therefor, has two meanings, a broad one and a narrow one. Generally, it is just a period during which a particular signal path for electrical signals representing ultrasonic signals is open. The narrow meaning or definition relates to the fact that for and during a specific looking window specific signals are expected to the exclusion of others.

It is customary in ultrasonic testing, for example, of sheet metal or other flat objects, to determine or to predetermine a particular period of time during which an echo pulse must be received so as to discriminate against other ultrasonic signals which could not possibly represent an echo by a defect or flaw in the material. For example, that period of time or looking window must not extend beyond the instant of occurrence of an echo from the rear or back wall, boundary or surface of the object tested. The device which establishes the basis for such a looking window is called a monitor, e.g., a signal monitor, digital monitor, analog monitor, integrating monitor, depending on the type and mode of operation. The looking window is established or generated by such a monitor, for example, by means of test reflections derived from representative test or reference objects, and once established, the looking window remains invariant. By way of example, sheet metal, strips, tubes or pipes may be tested by using test heads which transmit ultrasonic waves transversely to the surfaces of the test objects. For reasons of tolerances of the test objects, as well as of the test equipment, one can test only from the front surface of the test object down to a little (a few mm or less), above (inside) the rear or back wall surface; thus, the region near the rear wall surface must be excluded from inspection, i.e., the looking window for flaw echos must be closed well ahead of the occurrence of the rear wall echo.

The German printed patent application OS 24 22 439 discloses a method for automatic adjustment of the looking window, whereby echo pulses are measured and their occurrence controls the position (in time) of the looking window. This known method, however, has the disadvantage that it does not adjust to any differences in thickness of the test object. Thus, rear wall echos could be interpreted as a flaw echo, if the test object happens to be thin at the particular location. On the other hand, echos from flaws close to that rear wall may actually be missed for a thicker than normal location of the test object. These flaw signals, moreover, could influence the recognition of a reference echo, so that a wrong looking window is generated for subsequent measurements.

Another point to be considered is that one may test a sheet from both sides amounting to duplication of the equipment. Also, registration and association as well as cross checking of test data for purposes of ascertaining the true situation as to defects is quite difficult with the known equipment including, for example, compensation of the characteristics of the test heads, and referring to the respective rear wall echo.

DESCRIPTION OF THE INVENTION

It is an object of the present invention to provide an improved method for ultrasonic testing of objects which permits testing of the object from one side only, without having to exclude near surface regions.

It is a particular object of the present invention to improve the signal processing as resulting from ultrasonic tests and inspections of objects as to flaws, whereby respective previous test cycles are used to generate relevant data for succeeding cycles.

It is another particular object of the present invention to generate looking windows for flaw echos of ultrasonic test signals, and to track the generation of such looking windows on the basis of a preceding cycle or cycles.

In accordance with the preferred embodiment of the present invention, it is suggested to process echo signals originated pursuant to ultrasonic tests and inspection of an object in the following manner. In a particular cycle (which may be any measuring cycle or an initialization cycle), one detects occurrence of the first and second rear wall echos; the transit time difference yields representation of the thickness of the test object. In regard to the respective next test cycle, one generates three looking windows. The first one is to serve as a gating signal in the electrical path for signals representing the ultrasonic signals during which only flaw or defect echos could occur. That first window is to begin ahead of the first rear wall echo of that next cycle by said transit time difference, preferably, however, with a slight delay to exclude front wall echos. The first looking window is to end shortly before the expected first rear wall echo, and a second looking window for that latter echo is to begin shortly after the end of the first window. The second window ends preferably a constant period after its beginning. The third window begins at a delay following the end of the first window, the delay being preferably equal to said transit time difference; the third window lasts preferably also for a constant period.

In accordance with further improvements, the transit time of a flaw echo is referenced to a transit time that represents a smallest thickness for test objects. This smallest thickness may well be a hypothetical one. By shifting the end of the first window, it is possible to discriminate true rear near surface flaws from encroachment of the rear echo into the flaw detection, first window. Additionally, the contour of surface near flaws can readily be tracked.

This method can be practiced under utilization of appropriately programmed EDP equipment or through hardwire logic or by hand.

The invention can be practiced with normal test heads in which the direction of propagation of the ultrasonic signal from the respective transducer determines directly the direction of propagation in the test object, interpositioning of coupler fluid not withstanding. The signal processing described here can be used in conjunction with the method described in Ser. No. 764,763, now abandoned.

The invention can also be practiced with separate transmitter and receiver heads, being appropriately coupled, e.g., through water to the test object.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 2 is a function diagram for explaining the automatic adjustment of looking windows in accordance with the preferred embodiment of the invention.

Figure 1:
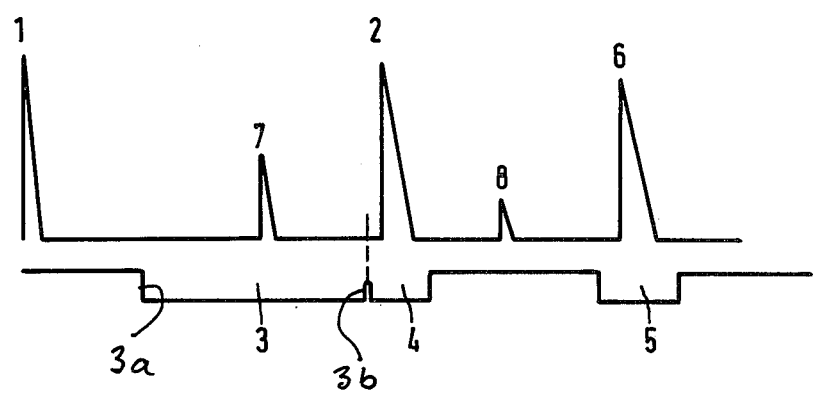
FIG. 1 is a simplified timing diagram for ultrasonic signals during one test cycle.

Proceeding now to the detailed description of the drawings, a single test cycle includes a transmitter pulse 1, a first rear wall echo pulse 2, and a second rear wall echo pulse 6, received after the first rear wall echo was in parts reflected back by the front surface and again reflected by the rear wall. The abscissa denotes time of occurrence of the respective pulse in the receiver in relation to the instant of transmitting the probing pulse 1. Signal peak 7 denotes by way of example, a reflection or echo of the transmitted probing signal by a defect, and signal peak 8 is a reflection by the same defect of that portion of the ultrasonic probing pulse which was first reflected by the rear wall, and that echo was again in parts reflected back by the front wall before being reflected by that defect.

In order to position (in time) the necessary looking window so that the flaw echo 7 (or other flaw echos) will be detected with certainty, one proceeds generally as follows. For each test cycle one ascertains the period between transmitted pulse 1 and first rear wall echo 2, in that, for example, a digital counter for constant rate clock pulses is triggered on occurrence of a pulse 1 and stopped on 2. The end 3b of the needed looking window 3 for the next test cycle is now set to occur from the transmit pulse 1 of the next test cycle by a delay given by the difference between the metered (counted) period and by a fixed tolerance, being, e.g., equal to the time it takes an ultrasonic signal to traverse the distance of about 0.3 mm in the test object material (e.g. steel). The end 3b will thus occur just prior to the expected occurrence of the rear wall echo in this next cycle.

The beginning 3a of the looking window 3 for that next test cycle is determined by ascertaining the actual thickness of the test object right at that point of inspection. This thickness is given by measuring the period (e.g. through pulse counting) between first (2) and second (6) rear wall echos. The beginning of the looking window 3 is now adjusted by determining the difference between the propagation period from transmission of pulse 1 and the first rear wall echo, and the propagation period between first and second rear wall echos, 2 and 6 respectively. Window 3 thus opens at that difference period after pulse 1 of the next cycle.

It should be noted that by ascertaining the beginning of the looking window 3 for any test cycle from the rear wall echos of the preceding cycle, any change, for example, in the length of the fluid coupler path between test head and test object, is automatically balanced.

In addition, two particular additional looking windows are calculated, denoted 4 and 5. These windows are opened or better, are to be opened for the two rear wall echos themselves. Window 4 begins very shortly after window 3 ends, and window 5 begins at a delay from end 3b of window 3 equal to the transit time 2-6 as metered. Windows 4 and 5 end at fixed periods after their beginnings. Therefore, the inventive method creates and tracks three looking windows 3, 4, 5, respectively, for separate and distinct flaw and rear wall echo detection, and the actual detection of rear wall echos in looking window periods 4 and 5 is used to track the windows for the next cycle.

FIG. 2 illustrates a sequence of steps in accordance with the inventive method and in greater detail. The diagram can be regarded as a program chart to be carried out by computing and processing facilities of the type well known in the art. The inputs to this facility (e.g. a minicomputer microprocessor, etc.) are the pulses 1, 2 and 6, derived from ultrasonic test equipment. These pulses are set into separate signal paths in the test equipment, opening of the signal paths for rear wall echos 2 and 6 is the purpose of generating the distinct looking windows 4 and 5. These pulses 2 and 6 may generate separate interrupts in the processor to obtain the counting processes outlined above for purposes of metering the periods between these pulses. Alternatively, the pulses 2 and 6, in addition to 1, may operate counters, and only the count results are acquired by the processor. Actual occurrence of rear wall echos during the respective windows may, however, be used and needed by the processor in executing its program as will be shown below.

The operation starts in that upon entry 9 into this routine preliminary looking windows 3, 4, 5, are used as initial parameters, and on the basis of past experience or separate test measurements one uses representative reference samples or the like. Block 10 denotes this initialization. The logic device or processor, therefor, furnishes gating signals for purposes of generating initial looking windows 3, 4, 5, for a first test cycle, and applies them to the above mentioned separate signal paths for the electrical signals produced in the test equipment upon receiving ultrasonic signals. The first test cycle uses these windows, particularly 4 and 5, to detect the first and second actual rear wall echos of a particular location of the test object.

The system now determines sequentially whether an echo signal is in window 3 (block 11) and whether echos are in windows 4 and 5 (block 12). If a signal is detected in window 3, one does not know at that point whether it is an echo from a flaw or the first rear wall echo. Please note that windows 3 and 4 are very close together. Thus, initially, one will try to find a location on the test object that is flaw free represented by absence of an echo in 3, presence of echos in 4 and 5 (at least in one of them). This initial test cycle is repeated until one finds such a location. If initially there are no echos in 4 and/or 5, then obviously the initialization parameters were wrong and have to be corrected.

Assuming that tests 11 and 12 did not cause a need for any or any further repeating, the next test cycle will be carried out at the same location and is used to undertake (or to acquire the metering of the periods 1-2, and 2-6 (block 13). The processor now calculates new specific values for the generation of a new looking window; gating signal 3 act as output of the processor to the one signal path (block 14). This calculation amounts specifically to the calculation of the time in which the window 3 is to be opened, following the transmitter pulse of the next test cycle and the time for which the window 3 is to be closed. As stated, the beginning 3a of the window 3 is given by the difference between the transit time periods 1-2 and 2-6, but at a slight delay to avoid a front wall echo to occur during the window 3. The end 3b of window 3 is given by a small constant period ahead of the time, the time rear wall echo 2 of the next cycle is expected to occur, which is given by the transit time 1-2 just metered shortened by a slight delay. The windows 4 and 5 are also generated as outlined earlier and with reference to the time 3b for the end of the flaw detect looking window.

The new values so calculated are, however, not used immediately. Rather, it is tested first (15) whether or not the resulting calculated duration of window 3 is shorter than a time that corresponds to the minimum thickness of any test object for which the method can be practiced. If that is so (15-yes), then the end 3b is set to occur at a time after the beginning equal to that minimum thickness time (block 16).

A "no" exit (23) from the test as per block 15 actually triggers the next text cycle during which it is determined whether or not a flaw echo occurs during looking window 3 (17). This is actually the first flaw detection cycle. If a flaw echo is not present, it is tested (20) whether a rear wall echo occurs in period 4. If that was, in fact, so, the program loops to the entry of the calculating subroutine as per block 13 to use that first true flaw detection cycle also for purposes of up-dating the looking windows.

Please note that the pulses 1, 2 and 6 via interruption or in a separate digital measuring circuit always meter the periods 1-2 and 2-6. Block 13 when executed within the program as described, can be regarded as a decision box whether or not to dump the metered periods or use them for new windows.

In any event, the loop 20 to 13 will eventually lead to a next measuring cycle following the no exit from 15, e.g. at a different location of the test object. Reaching of this entry point 23 can also be regarded as the trigger by the program for the next test cycle.

Assuming that test 20 was actually negative, this entails two aspects. First of all, new window data cannot possibly be derived from this cycle because absence of a rear wall echo during 4 leads inevitably to abortive attempts to meter these transit times 1-2 and 2-6. Secondly, therefor, the window calculation and updating is blocked for one, the next one, measuring cycle and another test cycle is initiated but using the window data as they were valid prior to this test cycle during which absence of a rear wall echo is detected. Thus, upon any updating the values which are used to generate new windows, the previous ones are not dumped but saved at least through the respective next test cycle, so that they can be reused.

Therefore, following a 21 to 17 branch, the next test cycle uses the old window data. Should that lead again to a 20-no test the program should best trap to take steps to remedy the situation, e.g. start anew at 9 for that location.

Up to now we have dealt only with the situation that a flaw or defect echo is not present, and is not detected in the looking window 3. If a defect echo does occur within a period that is in effect very close to the end 3b of the window, i.e., from a defect very close to the rear wall, it is possible that this "defect" pulse does not originate from a defect but is part of the leading edge portion of the rear wall echo in that intant; i.e., it is conceivable that for this test cycle the previously adjusted closing time or edge 3b of the looking window was shifted too close to the valid rear wall echo for that test location. "Very close" to the rear wall is to mean within a subsurface strata under the rear surface of the test object which has a thickness about equal to the smallest thickness of a test object for which the test method can be practiced (minimum thickness, supra).

Block 18 and the branch routines therefrom are designed to permit elimination of such incorrect flaw indication while aiding in the more precise locating of the flaw as detected. Therefore, test block 18 decides whether or not the flaw echo occurs in a particular period, representative of a minimum strata thickness of the test object, close, and in relation to the rear wall. If, in fact, the test has a positive answer, it is conceivable that the echo is part of the rear wall echo. Therefore, statement block 19 blocks window updating for one test cycle, and the program branches to entry point 23, for a repetition of the test under utilization of the previous window data. In other words, the test is repeated under the assumption that for this particular location now tested, the windows were adjusted incorrectly on the basis of the preceding test cycle.

If the detect echo within the period 3 was, in fact, a true echo, then this repetition test cycle should still yield another flaw detect situation as per inquiry 17. If that repeated test operation does not yield a flaw detection, then, indeed, the rear detected "flaw" was, in fact, a part of the rear wall echo, and the detected "flaw" is disregarded.

It should be noted, however, that independently from this actual repetition, one could (and should) compare the actual occurrences of (a) the rear wall echos of the test cycle that yielded the 18-yes result, and of (b) the rear wall echo from the preceding test. That difference (if any) is indicative of the possibility that the detected flaw was not a genuine one. If there is no difference in the rear wall echos in representation of the fact that the sheet or test object thickness is the same for the test, then the echo detected during 3 was, in fact, a flaw. The repeat cycle following 18-yes-19-23 will use the same end 3b of window 3, because the now by-passed updating did, in fact, very little to change the position of window end 3b.

The answer of the test 18 may be a negative one which could occur on the first detection of the flaw echo or after the repetition as just mentioned on account of the 18-yes branch operation because the branch 18-yes-19-23, under bypass of the last window update, may have caused the flaw echo to be shifted deeper into (earlier in) the window 3. Now, the detected transit time and occurrence of the flaw echo is used as the closing time (3b) for the next window 3. In other words, the next cycle will use an artificially shortened window 3 to see whether or not the flaw now vanishes. Alternatively, if one conducts that test at a slightly different location, one can now measure very accurately the oblique orientation of a defect. This is particularly true, if earlier the 18-no occured on a repetition test following an 18-yes result of the test as per block 18.

It can thus be seen that by providing a border line test as per 18, and by shifting on subsequent tests the window end 3b as well as tests tacked thereto, surface near defects can well be located, tracked, on their contour be determined.

The invention is not limited to the embodiments described above but all changes and modifications thereof not constituting departures from the spirit and scope of the invention are intended to be included.

We claim:

1. In a method of processing electrical signals which represent ultrasonic signals, generated pursuant to testing of an object as to flaws by transmission thereto of ultrasonic signals and detecting echos, whereby in each instance and test cycle, at least two echo pulses from the rear wall surface of the object are detected, comprising the steps of:

detecting the transit time of a first and a second rear wall pulse during a particular cycle and forming the transit time difference;

generating a first looking window for the detection of flaw echos during a cycle following the particular cycle, by providing for a beginning of the window at an instant ahead of the first rear wall echo by about said difference and by providing for an end of that window ahead of said first rear wall echo by a particular, relatively small amount;

generating a second looking window of predetermined width for detecting a first rear wall echo in the said following cycle, shortly after the end of said first window as generated;

generating a third looking window of predetermined width for detecting a second rear wall echo in the said following cycle, the third looking window beginning at a delay after the end of the first window as generated, the delay being said transit time difference, so that first and second rear wall echos can be distinguished from any flaw echo; and using the first and second rear wall echos as actually occuring during the second and third windows as generated, for the generation of the first looking window in the next following cycle as per said generating step.

2. In a method as in claim 1, wherein the beginning of said first window is delayed by corrective constant period to eliminate surface echos.

3. In a method as in claim 1, and including the step of repeating a test cycle in response to a flaw echo detected in the first window, thereby generating a first window whose end is phase shifted as compared with the first window in which the flaw echo was detected.

4. In a method as in claim 3, wherein a repeated cycle was a modified end of the respective first window to eliminate occurrence of a portion of a rear wall echo in the first window.

* * * * *